Figure 1:
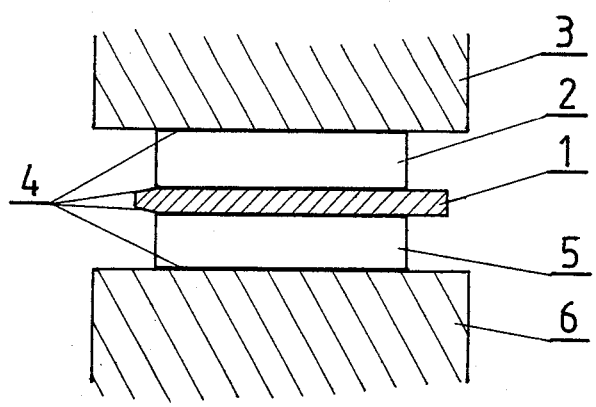

United States Patent [19]

Piórkowska-Palczewska et al.

[11] Patent Number: 4,630,938
[45] Date of Patent: Dec. 23, 1986

[54] METHOD OF DETERMINATION OF THERMAL CONDUCTION COEFFICIENT AND HEAT CAPACITY OF MATERIALS AND THE APPARATUS FOR MEASUREMENTS OF THERMAL CONDUCTION COEFFICIENT AND HEAT CAPACITY OF MATERIAL

[75] Inventors: Ewa Piórkowska-Palczewska; Andrzej Gałeski; Marian Kryszewski, all of Lódź, Poland

[73] Assignee: Polska Akademia Nauk Centrum Badan Molekularnych i Makromolekularnych, Lódź, Poland

[21] Appl. No.: 603,559

[22] Filed: Apr. 24, 1984

[30] Foreign Application Priority Data

Apr. 27, 1983 [PL] Poland ............................. 241663

[51] Int. Cl.⁴ ............... G01N 25/00; G01N 25/16; G01K 17/00
[52] U.S. Cl. ............................. 374/44; 374/43; 374/29
[58] Field of Search ......................... 374/29, 43, 44

[56] References Cited

U.S. PATENT DOCUMENTS 3,279,239 10/1966 Arends et al. ..................... 374/44
3,733,887 5/1973 Stanley et al. ..................... 374/44
3,971,246 7/1976 Sumikama ........................... 374/44

FOREIGN PATENT DOCUMENTS 173988 8/1965 U.S.S.R. .............................. 374/43

OTHER PUBLICATIONS

Andersson et al., "Thermal Conductivity of Solids Under Pressure by the Transient Hot Wire Method", Rev. Sci. Instrum., vol. 47, No. 2, Feb.-76, pp. 205-209.
Sandberg et al., "Heat Capacity and Thermal Conductivity from Pulsed Wire Probe Measurements Under Pressure", Journal of Physics E: Scientific Instrum., vol. 10, 1977, pp. 474-477.
Hager, Jr., Nathaniel, "Miniature Thin Heater Thermal Conductivity Apparatus", 5th Annual ISA Test Measurement Symposium, N.Y., Oct. 1968.
Dynatech Corporation, "Guarded Hot Plate Thermal Conductivity Measuring System", Model TCFGM Series, Mar. 1967.
Markman, M. A. et al., "Apparatus for the Rapid Measurement of Thermal Conductivity of Thermoelectric Materials", Ind. Lab. (USA) vol. 37, No. 10, Oct. 1971.
Grunert, W. E. et al., "Guarded Flat Plate Thermal Conductivity Apparatus for Testing Multi-Foil Insulations in the 20° C.-1000° C. Range", 9th Conf. on Thermal Cond., Ames, Iowa, Oct. 1969.

Primary Examiner—Charles Frankfort
Assistant Examiner—Thomas B. Will
Attorney, Agent, or Firm—Ladas & Parry

[57] ABSTRACT

A method and apparatus for determination the thermal conduction coefficient and the heat capacity of materials. The method comprises the measurements of heat flux across the sample and the momentary temperature difference between both surfaces of the sample perpendicular to the direction of heat flux during continuous change of the temperature of one of sample surfaces. The values of thermal conduction coefficient, heat capacity and thermal diffusivity are determined on the basis of an equation which defines their dependence on measured heat flux across the sample, temperature difference between the sample surfaces and the rate of the change of the temperature of one sample surface. The apparatus for measuring thermal conductivity and heat capacity contains a heater equipped with a temperature sensor of a thickness less than 1 mm, placed between two samples, one of them being the sample of material tested of a thickness less than 10 mm. The samples are in thermal contact with a flowing gas or liquid stream constituting heat sinks for the samples. The temperature of the flowing medium is changed linearly with time during each measurement run.

7 Claims, 2 Drawing Figures

METHOD OF DETERMINATION OF THERMAL CONDUCTION COEFFICIENT AND HEAT CAPACITY OF MATERIALS AND THE APPARATUS FOR MEASUREMENTS OF THERMAL CONDUCTION COEFFICIENT AND HEAT CAPACITY OF MATERIAL

The subject of the invention is the method of determination of thermal conduction coefficient and heat capacity of materials and the apparatus for measurements of thermal conduction coefficient and heat capacity of materials.

Thermal conduction coefficient is one of the most important parameters of materials from the theoretical and practical point of view. Heat transport controls all physical, physicochemical and chemical processes in the course of which the heat of the reaction or transition is generated.

Thermal conduction coefficient $\gamma$ is defined by the equation:

$$\frac{dQ}{dS} = -\lambda \operatorname{grad} T \tag{1}$$

where Q is the heat flux in the time unit across the surface S, T—the temperature.

Spatial changes of the heat flux are described by the equation:

$$\operatorname{div} \frac{dQ}{dS} = -c \frac{\partial T}{\partial t} \tag{2}$$

where c is the heat capacity of the material at the given experimental conditions.

Eqs. (1) and (2) fully describe the state of the material, i.e. the temperature distribution and heat fluxes within the material. Combination of eqs. (1) and (2) leads to the equation of thermal conductivity:

$$\frac{\partial T}{\partial t} = \frac{\lambda}{c} \nabla^2 T. \tag{3}$$

In the above equation there are two material parameters, c and $\gamma$. In the widely applied principle of experimental determination of the thermal conduction coefficient, based on eq. (1), said equation is taken to be independent on time i.e. steady-state conditions are considered.

Several constructions of the apparatus for determination of thermal conduction coefficient in steady-state conditions are known. An example of such construction is found in the U.S. Pat. No. 3,733,887 in which the apparatus consisting of the heating element placed between two samples of the material studied and connected to the temperature stabilizing device. The samples are in thermal contact with heat sinks.

In all known cases the constructions are based on the principle of determination of thermal conduction coefficient by measurements of the heat flux flowing across the material sample at the controlled temperature difference or by measurements of the temperature difference resulting from the flow of known heat flux. The results obtained from such measurements contain however several experimental errors. Said errors are usually caused by the transversal temperature gradient present in the samples which leads to heat dissipation outwards the experimental setup by heat convection and radiation.

Elimination of such errors in known constructions is usually, achieved by: using the samples in the form of plates, thickness of which is low in comparison with their lateral dimensions, applying the heated guard rings which eliminate the transversal temperature gradient in the samples, vacuuming the measuring setup in order to eliminate the heat dissipation by convection. Often the symmetrical measuring systems as e.g. described in cited above U.S. Pat. No. 3,733,887 are used which also permits reducing the aforementioned errors.

Determination of the thermal conduction coefficient requires applying the temperature difference between two opposite surfaces of the sample. Considering that the said temperature difference is usually of order of several Kelvins, the temperature at which $\gamma$ is determined is not precisely given.

The determination of the temperature difference at the constant heat flux or of the heat flux at constant temperature difference is made at stationary heat flow conditions which are reached in known constructions within several minutes or hours.

It is possible to determine the thermal conduction coefficient by the measurements of so called thermal diffusivity which is equal to the ratio of the thermal conductivity coefficient to the heat capacity. The measurement consists in the determination of time of flight of heat pulse across the layer of the material. There are known two methods of the determination of thermal diffusivity: "hot wire" method (Sandberg, Anderson, Bäckström; J. Physics E.Sci.Instr. 10, 474, 1977) and "flash" method (Chen, Poon, Choy; Polymer 18, 129, 1977), (Chang, Bestul; J.Chem.Phys. 55, 503, 1972), (Parker, Jenkins, Butler, Abbott; J.Appl.Phys. 32, 1679, 1961). In all these methods the temperature of the sample is controlled and the thermal conduction coefficient $\gamma$ is ascribed to some certain temperature close to the average temperature of the sample during the measurement.

Quasi-stationary method of thermal conduction coefficient measurement is also known (Eiermann, Hellwege, Knappe; Kolloid Z. 174, 134, 1961) in which the sum of temperature differences arising between the opposite surfaces of two flat samples due to heat flow to the colder metal plate placed between said samples is determined. Under the arbitrary assumption of temperature gradient linearity within the samples the thermal conductivity near the average temperature of the sample is given by the formula:

$$\lambda = mc_1 \frac{1}{S} \frac{\frac{dT}{dt}}{\Delta T_1 + \Delta T_2} \tag{4}$$

where m is the mass of the metal plate between the samples, $c_1$ is its specific heat, l is the thickness of the samples, $\Delta T_1$ and $\Delta T_2$ are the temperature differences between both sides of the samples, $$\frac{dT}{dt}$$

is the temperature change rate of the metal plate. In that construction the transversal gradient is eliminated by using the heated guard ring, convection and heat dissipation outwards the measuring unit is limited by placing the measuring unit in vacuum and by using two samples arranged in symmetrical system. Some limitations of this method follow from the assumption of linearity and time independence of the temperature gradient inside the samples. These assumptions are not necessarily fulfilled in the case of said method.

In the method according to the present invention the momentary temperature difference $\Delta T$ between both surfaces of the sample which are perpendicular to the direction of heat flux is measured during an applied continuous (preferably linear) change of the temperature of one of the sample surfaces. The method requires also the simultaneous measurement of the amount of heat which is supplied to the opposite surface of the sample in order to give rise to the said heat flux across the sample. The thermal conduction coefficient is determined on the basis of the relation:

$$\lambda = \frac{(2Q - blc)l}{2\Delta T} \quad (5)$$

where $\gamma$ is the thermal conduction coefficient, Q is the heat flux flowing across the sample in the time unit, $\Delta T$ is the temperature difference between both sides of the sample, c is heat capacity of the material, l is thickness of the sample, b is the rate of linear temperature change of one of the sides of the sample. On the basis of eq. (5) it is also possible to determine the heat capacity c of the material. The measurements can be carried out at different rates of temperature change. The required temperature change of one of the sample surfaces may be performed either directly or by putting it in thermal contact with highly heat conductive solid body, temperature of which is changed in the desired manner.

The apparatus for the thermal conduction coefficient measurement described in the present invention comprises thin layer measuring element, thickness of which is preferably lower than 1 mm, which is placed between two samples of the studied material. The said measuring element comprises thin layer heater placed between two thin layer temperature sensors. The samples of thickness preferably below 10 mm are in thermal contact with the heater and with the heat sinks which temperature is changed continuously with time during the measurements. One of the samples may be the standard reference sample. The thermal contacts are ensured with the aid of suspension of fine metal flakes in a lubricant. The solid heat sinks may be replaced with the stream of gas the temperature of which is controlled according to the required program. The construction according to the present invention permits the continuous measurements of the following quantities as the functions of temperature: thermal conduction coefficient, heat capacity, thermal diffusivity.

Performing the measurement requires determining the momentary temperature difference between two opposite surfaces of one of the samples and measuring the heat flux flowing across the sample. The temperature of the heat sinks being in contact with the samples is changed with time, preferably linearly, by means of a heating-cooling system controlled by an electronic programmable temperature controller (not shown). Transversal temperature gradient elimination is achieved by using flat samples, thickness of which is small in comparison to their transversal dimensions, and by means of the heated guard ring. Convection and heat dissipation are eliminated by using two samples placed on both surfaces of the heater.

More detailed description of the invention involving the example of apparatus construction shown schematically in FIG. 1 and some theoretical considerations defining the experimental conditions is given below along with FIG. 2 in which values of functions for typical polymers are plotted.

The method of continuous measurement of thermal conduction coefficient, heat capacity and thermal diffusivity requires the continuous measurement of the temperature difference between the opposite surfaces of the sample. The measurement is carried out in the system arranged symmetrically, i.e. two samples placed between two copper (or silver) plates are separated by the measuring element consisting of a thin layer heater and thin layer temperature sensors. Temperature of copper plates is linearly decreased or increased with time. Temperature within the sample is a function of time and coordinate, $T = T(x,t)$ and obeys the partial differential equation:

$$\nabla^2 T - \frac{c}{\lambda} \frac{\partial T}{\partial t} = -\frac{A}{\lambda} \quad (6)$$

where $\gamma$ is thermal conduction coefficient of the material and c is its heat capacity. Function $A = A(x)$ describes the heat generation in the heater and is equal to:

$$A(x) = -\frac{P}{2s} \delta(x - l) \text{ for } 0 \leq x \leq l \quad (7)$$

$$A(x) = -\frac{P}{2s} \delta(x - l) \text{ for } l \leq x \leq 2l$$

where $\delta$ is a Dirac function, P is the power supplied to the heater and s is the surface of the heater.

Equation (6) in the case of initial temperature $T_o = 0°$ is characterized by initial and boundary conditions:

$$T(x,0) = ax \text{ for } 0 \leq x \leq l \quad (8)$$

$$T(x,0) = a(2l - x) \text{ for } l \leq x \leq 2l$$

$$T(0,t) = bt$$

$$T(2l,t) = bt$$

$$T(0,0) = 0$$

where $$a = \frac{P}{2\lambda s},$$

b is the temperature change rate.

The equation (6) can be solved by the method of separation $$T(x,t) = U(x,t) + \omega(x,t)$$

Function $U(x,t)$ obeys the equation $$^2U - \frac{c}{\lambda} \frac{\partial U}{\partial t} = -\frac{1}{\lambda} A \quad (9)$$

having the initial and boundary conditions:

$$U(x,0) = ax \text{ for } 0 \leq x \leq l$$

$$U(x,0) = a/2l - x/ \text{ for } l \leq x \leq 2l$$

-continued $$U(0,t) = 0$$

$$U(2l,t) = 0$$

Furthermore, function U(x,t) can be split in two parts:

$$U(x,t) = U_1(x,t) + U_2(x,t) \tag{10}$$

function $U_1(x)$ obeys the equation below:

$$\nabla^2 U_1 = -\frac{1}{\lambda} A \tag{11}$$

with the boundary conditions:

$$U_1(0) = U_1(2l) = 0$$

$$U_1(l) = al$$

The solution of eq. (11) is in the form:

$$U_1 = ax \text{ for } 0 \leq x \leq l$$

$$U_1 = a(2l-x) \text{ for } l \leq x \leq 2l$$

Function $U_2(x,t)$ obeys the following equation:

$$\nabla^2 U_2 - \frac{c}{\lambda} \frac{\partial U_2}{\partial t} = 0 \tag{12}$$

with the conditions:

$$U_2(0,t) = 0$$

$$U_2(2l,t) = 0$$

and hence is equal to 0 for all values of x and t.

Function $\omega(x,t)$ is the solution of the following equation:

$$\nabla^2 \omega - \frac{c}{\lambda} \frac{\partial \omega}{\partial t} = 0 \tag{13}$$

with conditions:

$$\omega(x,0) = 0$$

$$\omega(0,t) = bt$$

$$\omega(2l,t) = bt$$

The solution of eq. (13) is in the form:

$$\omega(x,t) = bt - bF(x,t) \text{ for } 0 \leq x \leq 2l \tag{14}$$

Function T(x,t) is the superposition of functions $U_1$, $U_2$ and $\omega$:

$$T(x,t) = ax + bt - bF(x,t) \text{ for } 0 \leq x \leq l \tag{15}$$

$$T(x,t) = a(2l-x) + bt - bF(x,t) \text{ for } l \leq x \leq 2l \tag{15}$$

where:

$$F(x,t) = \frac{16l^2 c}{\pi^3 \lambda} \sum_{n=1}^{n=\infty} \frac{1}{(2n-1)^3} \sin\left(\frac{(2n-1)\pi x}{2l}\right) \left[1 - \exp\left(-\frac{\lambda(2n-1)^2 \pi^2 t}{4l^2 c}\right)\right]$$

The term (ax+bt) in eq. (15) describes the linear temperature gradient in the sample, temperature of which is changed linearly at a rate b with time.

Function F(x,t) represents the delay in the temperature change of the sample in the point at a distance x with respect to the applied, linear with time, change of temperature, this delay being caused by the heat capacity of the sample. Function F(x,t) has the property:

$$F(x,\infty) = \frac{16l^2 c}{\pi^3 \lambda} \sum_{n=1}^{\infty} \frac{1}{(2n-1)^3} \sin\left(\frac{(2n-1)\pi x}{2l}\right) \tag{16a}$$

$$F(0,\infty) = F(2l,\infty) = 0 \tag{16b}$$

$$F(l,\infty) = \frac{l^2 c}{2\lambda} \tag{16c}$$

Figure 2:
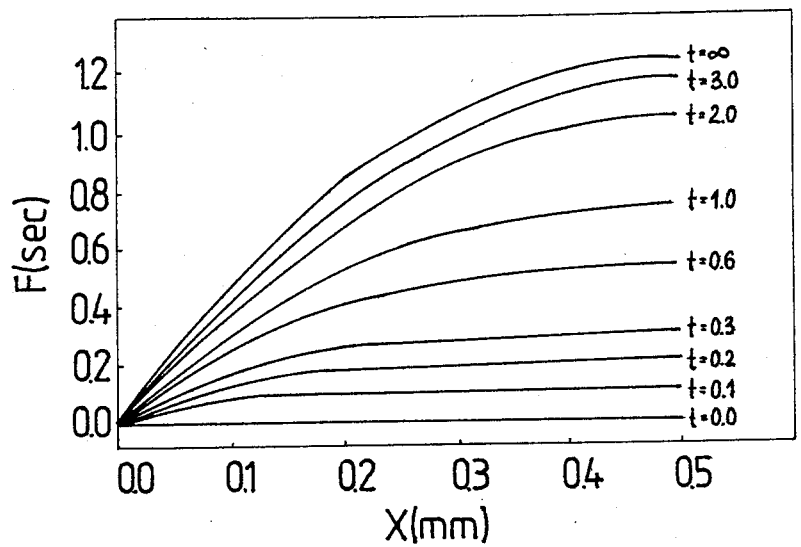

The plot of F(x,t) as a function of distance x calculated for various times t taking values of $\gamma$ and c typical for most polymers $$\left(\lambda = 0.2 \frac{W}{m \, deg} \quad c = 2 \text{ J/cm}^3 \text{deg}\right)$$

and the sample thickness 0.5 mm is shown in FIG. 2. As it is seen, after few seconds said delay no longer changes significantly and after this time lag it can be treated as a constant. The temperature difference $\Delta T$ between two sample surfaces arising during the measurement can be calculated from eq. (15). According to the previous considerations, if the temperature change rate b is sufficiently low, the values of F(x,t) may be replaced there with the values $F(x,\infty)$ given for sample surfaces by eqs. (16b) and (16c) and the obtained equation may be solved with respect to $\gamma$. Such a procedure leads to the following formula describing the thermal conduction coefficient $\gamma$ of the material in the form of two samples, both of thickness l and surface area s, separated by the heater supplied with power P causing the heat flow across them:

$$\lambda = \frac{(2Q - lbc)l}{2\Delta T} \tag{17}$$

In the equation $$Q = \frac{P}{2s}$$

denotes the heat flux across one of the samples, $\Delta T$ is the temperature difference between two surfaces of the sample, one of which is in thermal contact with the heater (which is placed between two samples) and the second with the heat sink.

Equation (17) may be also used for determination of the heat capacity of the material sample (in this case at least two measurements with different temperature change rates must be performed) and for determination of the thermal diffusivity (when no power is supplied to the heater placed between the samples).

Application of the described above method requires usage of the heating-measuring element 1, thickness of which should be sufficiently low in comparison to the thickness of the samples 2,5. The thinner said heating element is used the thinner samples may be studied. Thus, the method can be particularly advantageous if it is impossible to obtain thick samples of studied material without any structural deffects. It also permits studying small samples exhibiting an anisotropy of physical properties, which is important from both scientific and practical points of view.

One of the main technical problems in application of the said method is to ensure good thermal contacts between two samples 2, 5 and the heating-measuring element 1 and heat sinks 3, 6. This is particularly important when thin samples are used. Thermal contacts are usually achieved by application of liquid substances e.g. oil, fat, etc. However, at low temperatures, at which liquids solidify, thermal contacts become less efficient. Eierman, Hellwege and Knappe (Kolloid Z., 174, 134 (1961) have proposed to use gaseous helium to improve the thermal contacts within the measuring system. In the present invention the suspension of metal powders or flakes 4 in lubricant is applied. The introduction of suspension of metal powders or flakes ensures thermal contacts via metal particles and lubricant matrix at temperature at which the lubricant is viscous and via metal particles (or flakes) after solidification of lubricant. Applied linear change of the temperature is achieved in the system by means of a gas stream, the temperature of which is controlled by an electric heater (not shown) supplied with current by an electronic temperature controller equipped with a temperature programmer (not shown). The gas stream is obtained by evaporation of liquid nitrogen. In such system the linear temperature runs in the range from near liquid nitrogen temperature up to $+170°$ C. are obtained easily.

The surfaces of the samples 2,5 of the material studied are in thermal contact with flowing stream of gas constituting the heat sinks by means of copper or silver plates or blocks on which the thin layer resistance thermometers are placed. One of them serves as a sensor for temperature measurements of the surface of the sample, and the second as the sensor for the programmable temperature controller, which controls the changes of the system temperature. Heating-measuring element 1 prepared using thin layer technique contains: heater, heating guard ring, resistace thermometers serving as sensors for controlling the power supplied to the guard ring and for temperature measurements at the surfaces of the samples 2,5 (i.e. those surfaces of the samples which are in contact with said element). All circuits are glued together with polyester resin to form flat, less than 200 $\mu$m thick, plate. The heater has a form of a circle of 12 mm in diameter, the inner and outer diameters of the heated guard ring are equal to 12.5 and 16 mm respectively. The response of electrical bridges measuring the temperature difference on both sides (surfaces) of the samples 2,5 and the temperature of heat sinks 3,6 can be recorderd on X-Y recorder and/or transmitted to the computer to processing the data. Small thickness of the heating-measuring element and its relatively small diameter permit performing the measurements of thermal conductivity, heat capacity and thermal diffusivity of thin samples in the form of plates, films and strips. In the apparatus described the appropriate high accuracy is ensured at temperature differences between both sides of the samples less than $1°$ C. Good thermal contacts are achieved due to application of suspension of aluminium or silver flakes in a silicon vacuum grease.

What is claimed is:

1. A method for the determination of the heat conduction coefficient, heat capacity and thermal diffusivity of a material sample, comprising the measurement of a heat flux Q across the sample and the measurement of a momentary temperature difference $\Delta T$ between first and second opposite surfaces of said sample, which method is characterized in that the momentary temperature difference $\Delta T$ between both surfaces of the sample perpendicular to the direction of said heat flux is measured during a preferably linear applied continuous change of the temperature of said first surface of said sample, and supplying an amount of heat by a heater directly to said second surface of said sample in order to give rise to the heat flux Q across the sample, measuring said amount of heat supplied, while the values of the thermal conductivity coefficient, heat capacity and thermal diffusivity are determined on the basis of the following equation:

$$\lambda = \frac{(2Q - b1c)1}{2\Delta T}$$

where
$\gamma$—thermal conductivity coefficient $Q = \frac{P}{2s}$ — heat flowing across the sample per time unit per surface area $s$, where $P$ is the power supplied to the heater c—heat capacity of the sample
l—thickness of the sample
b—rate of change of the temperature of said first surface of said sample.

2. A method according to claim 1, wherein said measurements are performed with various rates of temperature change of said first sample surface.

3. A method according to claim 1, wherein the applied continuous change of the temperature of said first sample surface is obtained by means of thermal contact with a flowing stream of gas or liquid, the temperature of which is continuously changed with time during the said measurement.

4. A method according to claim 3, wherein the thermal contact of said first sample surface with the flowing stream is obtained by means of a solid body of high thermal conductivity.

5. An apparatus for measuring the thermal conductivity coefficient and heat capacity of a material sample, comprising a thin measuring element containing a thin flat heater having planar surfaces and thin flat temperature sensors mounted on both surfaces of the heater, said element having a thickness less than 1 mm, and being placed between two material samples to be tested each having a thickness of less than 10 mm, which apparatus is characterized in that the samples are in thermal contact with heat sinks and the temperature of said heat sinks being changed linearly with time during the period of measurement.

6. An apparatus according to claim 5, wherein one of the samples is a sample of material to be tested and the second sample is selected from either a sample of the same material, or a standard reference sample.

7. An apparatus according to claim 5, wherein the heat sinks comprise a stream of flowing gas or liquid.

* * * * *